United States Patent [19]

Delevalleé et al.

[11] Patent Number: 4,567,198

[45] Date of Patent: Jan. 28, 1986

[54] ETHANETHIOATES AND MERCAPTOAMIDES AND USE THEREOF AS ANALGESIC AND ENKEPHALINASE INHIBITORY COMPOUNDS

[75] Inventors: Francoisè Delevalleé, Vincennes; Roger Deraedt, Pavillons Sous Bois; Odile Le Martret, Paris, all of France

[73] Assignee: Raussel Uclaf, Paris, France

[21] Appl. No.: 577,032

[22] Filed: Feb. 6, 1984

[30] Foreign Application Priority Data

Feb. 7, 1983 [FR] France .................................. 83-01863

[51] Int. Cl.⁴ .................... A61K 31/265; A61K 31/16; C07C 103/12; C07C 153/023

[52] U.S. Cl. ..................................... 514/513; 564/192; 564/218; 260/455 R; 514/625; 548/195

[58] Field of Search ............................... 564/192, 218; 260/455 R; 424/301, 320, 324; 514/513, 625

[56] References Cited

U.S. PATENT DOCUMENTS 3,093,146  6/1963  Kalopissis et al. .................. 564/192

Primary Examiner—Henry R. Jiles

Assistant Examiner—Robert C. Whittenbaugh

Attorney, Agent, or Firm—Bierman, Peroff, & Muserlian

[57] ABSTRACT

Novel analgesic and enkephalinase inhibiting compositions comprising an analgesically and enkephalinase inhibitory effective amount of at least one compound selected from the group consisting of a compound of the formula

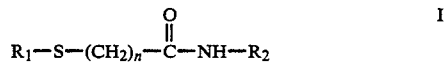

wherein $R_1$ is selected from the group consisting of hydrogen and acetyl, n is 1 or 2 and when n is 1, $R_2$ is selected from the group consisting of phenyl, p-chlorophenyl, m-trifluoromethylphenyl and thiazolyl and when n is 2, $R_2$ is selected from the group consisting of phenyl and p-chlorophenyl and their salts with non-toxic, pharmaceutically acceptable acids and bases and an inert pharmaceutical carrier and novel method of relieving pain and inhibiting enkephalinase activity in warm-blooded animals and novel amides.

10 Claims, No Drawings

ETHANETHIOATES AND MERCAPTOAMIDES AND USE THEREOF AS ANALGESIC AND ENKEPHALINASE INHIBITORY COMPOUNDS

U.S. Pat. No. 4,053,651 describes certain mercaptoacylamino acids useful for treatment of angiotensin related hypertension and U.S. Pat. No. 4,329,495 describes 2-(2-benzyl-3-mercaptopropionylamino)-1-alkanols and 2-(2-benzyl-3-mercaptopropionylamino)-4-methylthiobutyric acids having enkephalinase inhibition activity. U.S. Pat. No. 4,327,111 describes N-substituted-mercaptopropionamides which inhibit mammalian collagenase. EPO application No. 1,989 describes substituted mercapto acid amides useful to correct an imbalance of immune homeostasis and EPO application No. 38,758 describes amino acid derivatives having analgesic, hypotensive and enkephalinase inhibiting activity. U.S. Pat. No. 3,770,824 describes N-(4-chlorophenyl)-2-mercapto-acetamide and U.S. Pat. No. 3,878,248 describes N-(3-trifluoromethylphenyl)2-mercapto-acetamide. U.S. Pat. No. 2,709,706 describes N-phenyl-3-mercapto-propanamide. The said references describe pesticidal, herbicidal or insecticidal activity. Agra. Univ. J. Res. Sci., 1979 (pub. 1981), Vol. 28 (3), p. 139–142 describes N-(2-thiazolyl-2-mercapto-acetamide as a chemical compound. The above references don't describe any physiological activity for the said compounds.

OBJECTS OF THE INVENTION

It is an object of the invention to provide novel analgesic and enkephalinase inhibiting compositions and novel methods of relieving pain and inflammation in warm-blooded animals.

It is another object of the invention to novel ethanethioates.

These and other objects and advantages of the invention will become obvious from the following detailed description.

THE INVENTION

The novel compositions of the invention are analgesic and enkephalinase inhibiting compositions comprising an analgesically and enkephalinase inhibitory effective amount of at least one compound selected from the group consisting of a compound of the formula

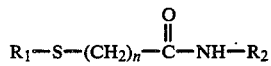

wherein $R_1$ is selected from the group consisting of hydrogen and acetyl, n is 1 or 2 and when n is 1, $R_2$ is selected from the group consisting of phenyl, p-chlorophenyl, m-trifluoromethylphenyl and thiazolyl and when n is 2, $R_2$ is selected from the group consisting of phenyl and p-chlorophenyl and their salts with non-toxic, pharmaceutically acceptable acids and bases and an inert pharmaceutical carrier.

Enkephalinase is a dipeptidylcarboxypeptidase which specially hydrolyses methionine and leucine enkephaline between the third and fourth amino acid liberating the tripeptide Tyr-Gly-Gly [Swerts et al, Europ. J. Pharmacol. Vol. 57 (1979), p.297]. Enkephalinase thus participates directly in the physiological degradation of enkephalines, natural endogenic ligands to opiaced receptors and the compounds of formula I which retard the degradation of enkephalines stimulate the defense reactions of organism against pain.

Examples of non-toxic, pharmaceutically acceptable acids for the formation of salts of the compounds of formula I are inorganic acids such as hydrochloric acid, hydrobromic acid, nitric acid, phosphoric acid and sulfuric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methanesulfonic acid and ethanesulfonic acid, aryl sulfonic acids such as benzene sulfonic acid and p-toluene sulfonic acid and arylcarboxylic acids.

Examples of non-toxic, pharmaceutically acceptable salts of bases are alkali metal salts such as those formed with sodium and potassium and amine salts such as those formed with triethylamine and dimethylamine.

Among the compounds of formula I useful for the compositions are N-phenyl-2-mercapto-acetamide, ethanethioate of S-[2-phenylamino-2-oxo-ethyl], N-(4-chlorophenyl)-2-mercaptoacetamide, ethanethioate of S-[2-(4-chlorophenylamino)-2-oxo-ethyl], N-(3-trifluoromethylphenyl)-2-mercapto-acetamide, N-phenyl-3-mercapto-propanamide, ethanethioate of S-[3-oxo-3-phenylaminopropyl], N-(4-chlorophenyl)-3-mercapto-propanamide, ethanethioate of S-[3-(4-chlorophenylamino)-3-oxo-propyl], N-(2-thiazolyl)-2-mercapto-acetamide and ethanethioate of S-[2-(2-thiazolylamino)-2-oxo-ethyl] and their salts with non-toxic, pharmaceutically acceptable acids and bases.

Especially preferred compositions of the invention are those containing as the active ingredient a compound selected from the group consisting of N-(4-chlorophenyl)-2-mercapto-acetamide, ethanethioate of S-[2-(4-chlorophenylamino)-2-oxo-ethyl], N-phenyl-3-mercapto-propanamide, N-(2-thiazolyl)-2-mercapto-acetamide and their salts with non-toxic, pharmaceutically acceptable bases and acids.

The compositions may be in the form of tablets, dragees, gelules, granules, suppositories, pomades, creams, gels, injectable solutions or suspensions or aerosols. Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions are useful for the treatment of muscular, articular or nervous pain, rhumatismal affections, dental pain, zonas and migraines as well as arthrosis, lumbagos and as a complementary treatment in infectious or feverish states.

The novel method of the invention for treating pain and inducing enkephalinase inhibiting activity in warm-blooded animals, including humans, comprises administering to warm-blooded animals an analgesically and enkephalinase inhibitory effective amount of at least one compound of formula I and their salts with non-toxic, pharmaceutically acceptable acids and bases. The compounds may be administered orally, rectally, parenterally or by topical application to the skin and mucous. The usual daily dose depends on the compound, the method of administration and the condition being treated. For example, an oral administration consists of 0,25 to 25 mg/kg per day.

The novel compounds of the invention are selected from the group consisting of ethanethioate of S-[2-(4-chlorophenylamino)-2-oxo-ethyl], ethanethioate of S-

[3-oxo-2-phenylaminopropyl], ethanethioate of S-[3-(4-chlorophenylamino)-3-oxo-propyl], ethanethioate of S-[2-(2thiazolylamino)-2-oxo-ethyl] and their salts with non-toxic, pharmaceutically acceptable acids and bases.

The compounds of formula I wherein n is 1 can be prepared by the process of J. Org. Chem., Vol. 37, No. 10 (1972), p. 1527 wherein mercapto-acetic acid or a functional derivative thereof is reacted with an amine of the formula $H_2N-R_2$ wherein $R_2$ has the above definition to obtain a compound of formula I wherein n is 1 and $R_1$ is hydrogen and optionally reacting the latter with acetyl chloride to form the compound of formula I wherein $R_1$ is

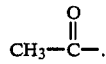

The compounds of formula I wherein $R_1$ is

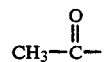

may be prepared directly by reacting an amine of the formula $H_2N-R_2$ wherein $R_2$ has the above definition with acetylthio-acetic acid [described in U.S. Pat. No. 2,412,700] or a functional derivative thereof.

The compounds of formula I wherein n is 2 may be prepared by an analogous procedure to that described in U.S. Pat. No. 4,053,651.

The salts of the compounds of formula I may be prepared by reacting approximately stoichiometric amounts of the compounds of formula I with the appropriate base or acid.

In the following examples there are described several preferred embodiments to illustrate the invention. However, it should be understood that the invention is not intended to be limited to the specific embodiments.

EXAMPLE 1

Ethanethioate of S-[2-(4-chlorophenylamino)-2-oxo-ethyl]

A solution of 7.65 g of N-(4-chlorophenyl)-2-mercaptoacetamide [described in J. Org. Chem., Vol. 37, No. 10 (1972), p. 1527] in 115 ml of tetrahydrofuran was added at less than 25° C. under nitrogen to a suspension of 2 g of sodium hydride in 19 ml of tetrahydrofuran and after hydrogen evolution ceased, 3.12 g of acetyl chloride were added to the mixture. The mixture was stirred at 20° C. for one hour and then 570 ml of ether and 190 ml of water were added thereto with stirring. The decanted organic phase was washed with water, dried, filtered and evaporated to dryness under reduced pressure. The 8.7 g of residue were chromatographed over silica gel and was eluted with methylene chloride to obtain 4.7 g of ethanethioate of S-[2-(4-chlorophenylamino)-2-oxo-ethyl] melting at 130° C.

EXAMPLE 2

Ethanethioate of S-[3-oxo-3-phenylamino-propyl]

STEP A: 3-acetylthio-propionyl chloride 100 ml (1.4 moles) of thioacetic acid were added over 30 minutes under argon at 22° to 35° C. with stirring to 75 ml (1.1 moles) of acrylic acid and the mixture was stirred overnight at room temperature and then at 100° C. for 90 minutes. The temperature returned to room temperature while crystals formed and excess thioacetic acid was removed under reduced pressure. The 170 g of crystals were dissolved in 170 ml of ether and 130 ml of thionyl chloride were added over 30 minutes with stirring under argon to the solution. The mixture was stirred overnight at room temparature and was evaporated to dryness under reduced pressure. Distillation of the oil residue at 0.5 Torr yield 146.9 g of 3-acetylthio-propionyl chloride with a boiling point of 63°–64° C. at 0.5 Torr.

STEP B: Ethanethioate of S-[3-oxo-3-phenylamino-propyl]

A solution of 16.5 g of aniline in 500 ml of methylene chloride was added with stirring at −35° C. under argon to a solution of 15.1 g of the product of Step A in 500 ml of methylene chloride and the mixture was returned to room temperature and stirred for 16 hours. The mixture was filtered to remove aniline hydrochloride and the filtrate was washed with 0.1N hydrochloric acid and then with water until the wash water was neutral. The wash waters were extracted twice with methylene chloride and the combined organic phases were dried, filtered and evaporated to dryness under reduced pressure. The 21.5 g of residue were triturated with 250 ml of pentane and was filtered and dried under reduced pressure to obtain 20 g of ethanethioate of S-[3-oxo-3-phenylamino-propyl] melting at 99° C.

EXAMPLE 3

Ethanethioate of S-[3-(4-chlorophenylamino)-3-oxo-propyl]

A solution of 4-chloroaniline in 250 ml of methylene chloride was added with stirring under argon at −35° C. over 45 minutes to a solution of 15.7 g of the product of Step A of Example 2 in 250 ml of methylene chloride and the mixture was stirred for 22 hours. The temperature was returned to room temperature and the mixture was filtered to remove 4-chloroaniline hydrochloride. The filtrate was washed with 0.1N hydrochloric acid and then with water, dried and evaporated to dryness under reduced pressure. The residual crystals were dissolved in methylene chloride and the solution was treated with activated carbon and was filtered. The filter was washed with methylene chloride and the filtrate was evaporated to dryness under reduced pressure. The 24.5 g of residue were triturated with a mixture of 100 ml of ether and 70 ml of pentane and was filtered. The product was empasted with a 6–4 ether-pentane mixture, filtered and dried under reduced pressure to obtain 22 g of ethanethioate of S-[3-(4-chlorophenylamino)-3-oxo-propyl] melting at 103° C.

EXAMPLE 4

Ethanethioate of S-[2-(2-thiazolylamino)-2-oxo-ethyl]

20.8 ml of triethylamine were added to a solution of 10 g of aminothiazole in 70 ml of ethyl acetate with cooling and a solution of 18.24 g of ethanethioate of S-[2-chloro-2-oxo-ethyl] [described in Chem. Ab., Vol. 41, p. 1702] in 20 ml of ethyl acetate were added there over 20 minutes at 20° to 30° C. The mixture was stirred at room temperature for 2 hours and was vacuum filtered. The product was washed with ethyl acetate and then was stirred with 150 ml of water and was filtered. The filtrate was washed with water, was vacuum filtered and evaporated to dryness under reduced pressure. The 19.3 g residue were crystallized from ethyl acetate to obtain 10.4 g of ethanethioate of S-[2-(2-thiazolylamino)-2-oxo-ethyl] melting at 183° C.

EXAMPLE 5

Tablets were prepared containing 50 mg of N-(4-chlorophenyl)-2-mercapto-acetamide or 200 mg of N-thiazolyl-2-mercaptoacetamide and sufficient excipient of lactose, starch, talc and magnesium stearate for a tablet weight of 350 mg.

PHARMACOLOGICAL DATA

A. Inhibition of Enkephalinase

Enkephalinase activity was determined in a striatum membrane fraction of rats. The straitum was placed in ice and was homogenized in buffered 0.05M Tris with a pH of 7.4 (20 times the volume) and after a first centrifugation at 1000 g, the particular fraction obtained was subjected to two centrifugations for 10 minutes at 20,000 g. The culot was then suspended in buffered Tris and kept at 4° C. The amount of proteins was determined by the Comassie blue method.

After preincubation at 25° C. for 15 minutes, an aliquot of proteins was incubated at 25° C. for 15 minutes in the presence of 20 nanomoles of tritiated leucine-enkephaline (against the first amino acid) previously purified, of 1 mM of puromycin and the test product in buffered Tris. The hydrolysis reaction was stopped by addition of 0.2N hydrochloric acid and the icubate was subjected to a deproteinization by heating at 95° C. for 15 minutes. Under these conditions, the kinetic reaction was linear. The tritiated metabolites obtained by hydrolysis were separated from enkephaline by chromatography over a column of porapak Q and elution with buffered Tris whereby enkephaline was retained in the column and was released in the following ethanolic phase. The activity of the different products was expressed in 50% inhibiting concentration called $CI_{50}$ in Table I.

TABLE I

| Product | Enkephalinase inhibition $CI_{50}$ in $10^{-5}$M |
| --- | --- |
| N—phenyl-2-mercapto-acetamide | 0.3 |
| N—(4-chlorophenyl)-2-mercapto-acetamide | 0.5 |
| ethanethioate of S—[2-(4-chloro-phenylamino)-2-oxo-ethyl] | 0.6 |
| N—phenyl-3-mercapto-propaneamide | 4 |
| N—(2-thiazolyl)-2-mercapto-acetamide | 3 |
| ethanethioate of S—[2-(2-thiazolyl-amino)-2-oxo-ethyl] | 13 |

B. Analgesic Activity

The test was a variation of the Randall et al test [Arch. Int. Pharmacodyn, Vol. 111 (1957), p. 409] wherein the analgesic activity was determined in rats by the threshold of sensitivity to pain lowered by an inflammation. The inflammation was obtained by injection of 0.25 mg of carraghenin in the plantary aponevrose of a rear paw and pain was provoked by a mechanical pressure applied to the right face of the paw and was increased regularly by an analgesimeter. The pain threshold was appreciated by the pressure necessary to release a reaction by withdrawing the paw or a vocal cry. The test products were administered by oral route four hours after the injection of carraghenin and the pain threshold was measured immediately before the injection of irritant and one hour after treatment. The results are reported in Table II.

TABLE II

| Product | DA in mg/kg |
| --- | --- |
| N—phenyl-2-mercapto-acetamide | >20 |
| N—(4-chlorophenyl)-2-mercapto-acetamide | 4 |
| ethanethioate of S—[2-(4-chloro-phenylamino)-2-oxo-ethyl] | 4 |
| N—phenyl-3-mercapto-propanamide | 4 |
| ethanethioate of S—[3-oxo-3-(phenylamino)-propyl] | 4 |
| N—(2-thiazolyl)-2-mercapto-acetamide | 4 |
| ethanethioate of S—[2-(2-thiazolyl-amino)-2-oxo-ethyl] | 4 |

Various modifications of the products and processes of the invention may be made without departing from the spirit or scope thereof and it is to be understood that the invention is to be limited only as defined in the appended claims.

What we claim is:

1. An analgesic and enkephalinase inhibiting composition comprising an analgesically and enkephalinase inhibitory effective amount of at least one compound selected from the group consisting of a compound of the formula

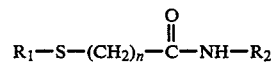

I wherein $R_1$ is selected from the group consisting of hydrogen and acetyl, n is 1 or 2 and when n is 1, $R_2$ is selected from the group consisting of phenyl and p-chlorophenyl, m-trifluoromethylphenyl and when n is 2, $R_2$ is selected from the group consisting of phenyl and p-chlorophenyl and their salts with non-toxic, pharmaceutically acceptable acids and bases and an inert pharmaceutical carrier.

2. A composition of claim 1 wherein the active ingredient is selected from the group consisting of N-phenyl-2-mercapto-acetamide, ethanethioate of S-[2-phenylamino-2-oxo-ethyl], N-(4-chlorophenyl)-2-mercapto-acetamide, ethanethioate of S-[2-(4-chloro-phenylamino)-2-oxo-ethyl], N-(3-trifluoromethyl-phenyl)-2-mercapto-acetamide, N-phenyl-3-mercapto-propanamide, ethanethioate of S-[3-oxo-3-phenylamino-propyl], N-(4-chlorophenyl)-3-mercapto-propanamide, ethanethioate of S-[3-(4-chlorophenylamino)-3-oxo-propyl], and their salts with non-toxic, pharmaceutically acceptable acids and bases.

3. A composition of claim 1 wherein the active ingredient is selected from the group consisting of N-(4-chlorophenyl)-2-mercapto-acetamide, ethanethioate of S-[2-(4-chlorophenylamino)-2-oxo-ethyl], N-phenyl-3-mercapto-propanamide, and their salts with non-toxic, pharmaceutically acceptable bases and acids.

4. A method of relieving pain in warm-blooded animals comprising administering to warm-blooded animals an analgesically effective amount of at least one compound selected from the group consisting of compound of the formula

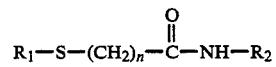

I wherein $R_1$ is selected from the group consisting of hydrogen and acetyl, n is 1 or 2 and when n is 1, $R_2$ is selected from the group consisting of phenyl, p-chlorophenyl and m-trifluoromethylphenyl and when n is 2, $R_2$ is selected from the group consisting of phenyl, p-chlorophenyl and m-trifluoromethylphenyl and their salts with non-toxic, pharmaceutically acceptable acids and bases.

5. The method of claim 4 wherein the compound is selected from the group consisting of N-phenyl-2-mercapto-acetamide, ethanethioate of S-[2-phenylamino-2-oxo-ethyl], N-(4-chlorophenyl)-2-mercapto-acetamide, ethanethioate of S-[2-(4-chlorophenylamino)-2-oxo-ethyl], N-(3-trifluoromethylphenyl)-2-mercapto-acetamide, N-phenyl-3-mercapto-propanamide, ethanethioate of S-[3-oxo-3-phenylamino-propyl], N-(4-chlorophenyl)-3-mercapto-propanamide, ethanethioate of S-[3-(4-chlorophenylamino)-3-oxo-propyl], and their salts with non-toxic, pharmaceutically acceptable acids and bases.

6. The method of claim 4 wherein the active compound is selected from the group consiting of N-(4-chlorophenyl)-2-mercapto-acetamide, ethanethioate of S-[2-(4-chlorophenylamino)-2-oxo-ethyl], N-phenyl-3-mercapto-propanamide, and their salts with non-toxic, pharmaceutically acceptable bases and acids.

7. A method of inhibiting enkephalinase in warm-blooded animals comprising administering to warm-blooded animals an enkephalinase inhibitory amount of at least one compound selected from the group consisting of compound of the formula

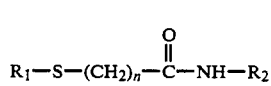

wherein $R_1$ is selected from the group consisting of hydrogen and acetyl, n is 1 or 2 and when n is 1, $R_2$ is selected from the group consisting of phenyl, p-chlorophenyl and m-trifluoromethylphenyl and when n is 2, $R_2$ is selected from the group consisting of phenyl, p-chlorophenyl and m-trifluoromethylphenyl and their salts with non-toxic, pharmaceutically acceptable acids and bases.

8. The method of claim 7 wherein the compound is selected from the group consisting of N-phenyl-2-mercapto-acetamide, ethanethioate of S-[2-phenylamino-2-oxo-ethyl], N-(4-chlorophenyl)-2-mercapto-acetamide, ethanethioate of S-[2-(4-chlorophenylamino)-2-oxo-ethyl], N-(3-trifluoromethylphenyl)-2-mercaptoacetamide, N-phenyl-3-mercapto-propanamide, ethanethioate of S-[3-oxo-3-phenylamino-propyl], N-(4-chlorophenyl)-3-mercapto-propanamide, ethanethioate of S-[3-(4-chlorophenylamino)-3-oxo-propyl], and their salts with non-toxic, pharmaceutically acceptable acids and bases.

9. The method of claim 7 wherein the active compound is selected from the group consisting of N-(4-chlorophenyl)-2-mercapto-acetamide, ethanethioate of S-[2-(4-chlorophenylamino)-2-oxo-ethyl], N-phenyl-3-mercapto-propanamide, and their salts with non-toxic, pharmaceutically acceptable bases and acids.

10. A compound selected from the group consisting of ethanethioate of S-[2-(4-chlorophenylamino)-2-oxo-ethyl], ethanethioate of S-[3-oxo-3-phenylamino-propyl], ethanethioate of S-[3-(4-chlorophenylamino)-3-oxo-propyl], and their salts with non-toxic, pharmaceutically acceptable acids and bases.

* * * * *